(12) United States Patent
Brown

(10) Patent No.: US 8,158,610 B2
(45) Date of Patent: *Apr. 17, 2012

(54) DEXTRIN-CONTAINING COMPOSITION FOR PREVENTING SURGICAL ADHESIONS

(75) Inventor: Colin Brown, Blaby (GB)

(73) Assignee: Innovata Limited, Chippenham, Wiltshire (GB)

( * ) Notice: Subject to any disclaimer, the term of this patent is extended or adjusted under 35 U.S.C. 154(b) by 0 days.

This patent is subject to a terminal disclaimer.

(21) Appl. No.: 12/800,105

(22) Filed: May 7, 2010

(65) Prior Publication Data

US 2010/0240607 A1 Sep. 23, 2010

Related U.S. Application Data

(63) Continuation of application No. 09/700,057, filed as application No. PCT/GB99/01306 on May 13, 1999, now Pat. No. 7,732,428.

(30) Foreign Application Priority Data

May 13, 1998 (GB) .................................. 9810127.2

(51) Int. Cl.
*A61K 31/718* (2006.01)
*C08B 30/18* (2006.01)

(52) U.S. Cl. .......................................... 514/58; 536/103

(58) Field of Classification Search .................... 514/58; 536/103
See application file for complete search history.

(56) References Cited

U.S. PATENT DOCUMENTS

| | | | |
|---|---|---|---|
| 4,886,789 A | 12/1989 | Milner | |
| 5,093,319 A | 3/1992 | Higham et al. | |
| 5,230,933 A | 7/1993 | Apfeld et al. | |
| 5,258,175 A | 11/1993 | Davies | |
| 5,280,017 A | 1/1994 | Davies | |
| 5,587,175 A | 12/1996 | Viegas et al. | |
| 5,837,060 A | 11/1998 | Fouache nee Ducroquet et al. | |
| 5,985,851 A | 11/1999 | Falk et al. | |
| 6,039,719 A | 3/2000 | Wieslander et al. | |
| 6,068,705 A | 5/2000 | Tang et al. | |
| 2003/0022861 A1 | 1/2003 | Conroy et al. | |
| 2003/0153529 A1 | 8/2003 | Conroy | |
| 2006/0134124 A1 | 6/2006 | Lechler et al. | |
| 2007/0009485 A1 | 1/2007 | Conroy et al. | |

FOREIGN PATENT DOCUMENTS

| | | |
|---|---|---|
| EP | 207676 | 1/1989 |
| EP | 815879 | 1/1998 |
| JP | 2-167042 | 6/1990 |
| JP | 9-000209 | 1/1997 |
| WO | WO90/10031 | 9/1990 |
| WO | WO92/21354 | 12/1992 |
| WO | WO96/15795 | 5/1996 |
| WO | WO96/40090 | 12/1996 |
| WO | WO96/40168 | 12/1996 |

OTHER PUBLICATIONS

Dobbie, JW. "Separation of Peritoneal Surfaces Through the Maintenance of an Artificial Ascites as a Preventative of Peritoneal Adhesions" abstract, from The 4th Peritoneum and Peritoneal Access Meeting, Sep. 16-19, 1997.*
DeWilde et al. Gynceol. Surg., 2007, 4, p. 243-253.*
Holtz, et al., Fertility and Sterility, vol. 33, No. 6, pp. 660-662 (Jun. 1980).
Holtz, et al., Fertility and Sterility, vol. 34, No. 4, pp. 394-395 (Oct. 1980).
Treutner, et al., J. Surg. Res., vol. 59, pp. 764-771 (1995).
Dobbie, Abstract from the 4th Peritoneum and Peritoneal Access Meeting, Sep. 16-19, 1997.
English Language Translation of Official Action in Japanese Patent Application No. 2000-548018, Jul. 18, 2003.
Harris, et al., Surgery, vol. 117, No. 6, pp. 663-669 (2005).

* cited by examiner

*Primary Examiner* — Shaojia Anna Jiang
*Assistant Examiner* — Jonathan S Lau
(74) *Attorney, Agent, or Firm* — Carella, Byrne, et al.; Elliot M. Olstein; Raymond J. Lillie

(57) ABSTRACT

A method of reducing the incidence of post-operative adhesions in or associated with a body cavity, which comprises introducing into the body cavity a composition containing an aqueous solution or suspension or gel formulation containing the polysaccharide dextrin.

44 Claims, No Drawings

DEXTRIN-CONTAINING COMPOSITION FOR PREVENTING SURGICAL ADHESIONS

This application is a continuation of application Ser. No. 09/700,057, filed Feb. 5, 2001 now U.S. Pat. No. 7,732,428, which is the national phase application of PCT Application No. PCT/GB99/01306, filed May 13, 1999, which claims priority based on U.S. patent application Ser. No. 09/272,713, filed Mar. 13, 1999, and United Kingdom Patent Application No. 9810127.2, filed May 13, 1998, the contents of which are incorporated herein by reference in their entireties.

This invention relates to the prevention of adhesions, and in particular to adhesions taking place in serous cavities including the peritoneum, the pericardium, the plura and synovial cavities such as joints and tendons and to adhesions following spinal and/or cranial operations. Reference will be made hereinbelow to the prevention of adhesions in the peritoneum but it should be understood that the present invention has applicability in connection with other serous cavities in both humans and animals.

Abdominal surgery is a rapidly changing field. Many forms of open surgery are being increasingly replaced by laparoscopic procedures. Although considerable immediate post-surgical benefits have been demonstrated to follow from laparoscopic surgery, the incidence of adhesions has not decreased. The severe drying of the mesothelium which results from prolonged exposure of the peritoneum to dry gases (pneumoperitoneum of 2-4 hours), may give rise to a higher incidence of global peritoneal adhesions than has hitherto been encountered in open surgery. Many gynaecologists with long experience of laparoscopic surgery consider that both open and closed surgery have equally high incidences of adhesions.

WO 92/21354 describes a surgical adhesion as the attachment of organs or tissues to each other through scar tissue. A formation of scar tissue is described as a normal sequel to surgery or other tissue injury and is required for proper wound healing. In some cases, however, the scar tissue overgrows the intended region and creates surgical adhesions. These scar tissue surgical adhesions restrict the normal mobility and function of affected body parts. The invention disclosed in WO 92/21354 is based on the discovery that anionic polymers effectively inhibit invasion of cells associated with detrimental healing processes, ie, fibrosis, and scaring. In particular, certain inhibitory anionic polymers are useful to inhibit fibroblast invasion, thus regulating the healing process and preventing fibrosis. Anionic polymers specified in WO 92/21354 include dextran sulfate, pentosan polysulfate as well as natural proteoglycans, or the glycosaminoglycan moieties of proteoglycans, including dermatan sulfate, chondroitin sulfate, keratan sulfate, heparan sulfate, heparin and alginate.

By attempting to inhibit fibroblast invasion, the approach of WO 92/21354 is one of post-adhesion treatment since fibroblast invasion is a later stage, that is to say, it occurs after formation of the adhesion. The invention of WO 92/21354 attempts to prevent the adhesion becoming permanent. By contrast the present invention is concerned with the prevention of the occurrence of an adhesion.

According to a first aspect of the present invention there is provided a method of preventing or reducing the incidence of post-operative adhesions in or associated with a body cavity, which comprises introducing into the body cavity an aqueous solution or suspension or gel formulation containing the polysaccharide dextrin.

The term "dextrin" means a glucose polymer which is produced by the hydrolysis of starch and which consists of glucose units linked together by means mainly of $\alpha$-1,4 linkages. Typically dextrins are produced by the hydrolysis of starch obtained from various natural products such as wheat, rice, maize and tapioca. In addition to $\alpha$-1,4 linkages, there may be a proportion of $\alpha$-1,6 linkages in a particular dextrin, the amount depending on the starch starting material. Since the rate of biodegradability of $\alpha$-1,6 linkages is typically less than that for $\alpha$-1,4 linkages, it is preferred that, for many applications, the percentage of $\alpha$-1,6 linkages is less than 10% and more preferably less than 5%.

Any dextrin is a mixture of polyglucose molecules of different chain lengths. As a result no single number can adequately characterise the molecular weight of such a polymer. Accordingly, various averages are used, the most common being the weight average molecular weight (Mw) and the number average molecular weight (Mn). Mw is particularly sensitive to changes in the high molecular weight content of a polymer whilst Mn is largely influenced by changes in the low molecular weight content of the polymer.

It is preferred that the Mn of the dextrin is in the range of from 1,000 to 30,000 and ideally the Mw is in the range of from 3,000 to 50,000. More preferably, the Mn is from 3,000 to 8,000 and the Mw is from 5,000 to 50,000.

The term "degree of polymerisation" (DP) can also be used in connection with polymer mixtures. For a single polymer molecule, DP means the number of polymer units. For a mixture of molecules of different DP's, weight average DP and number average DP correspond to Mw and Mn. In addition, DP can also be used to characterise a polymer by referring to the polymer mixture having a certain percentage of polymers of DP greater than a particular number or less than a particular number.

It is preferred that the dextrin contains more than 15% of polymers of DP greater than 12 and, more preferably, more than 50% of polymers of DP greater than 12.

The dextrin used in the present invention is water soluble or at least forms a suspension in water or a gel formulation. The dextrin used in this invention may be in the form of either unsubstituted dextrin (as obtained by the hydrolysis of starch) or may be substituted by one or more different groups. The substituents may be negatively charged groups, for instance, sulfate groups, neutral groups, or positively charged groups, for instance, quaternary ammonium groups. In the case where the substituent group is sulfate, it is preferred that the sulfated polysaccharide contains at least one sulfate group per saccharide (glucose) unit.

The present invention also provides a composition comprising an aqueous solution or suspension or gel formulation of the polysaccharide dextrin in which the amount of dextrin is effective to prevent or reduce the incidence of post-operative adhesions.

The present invention further provides the use of a composition in the prevention or reduction of the incidence of post-operative adhesions, the composition comprising a aqueous solution or suspension or gel formulation of the polysaccharide dextrin.

The present invention further provides the use of the polysaccharide dextrin in the manufacture of a composition comprising an aqueous solution or suspension or gel formulation of dextrin for preventing or reducing post-operative adhesions in humans and animals.

Dextrin is a useful material for the production of an adhesion-preventing composition because, inter alia, it is non-toxic, cheap and has the ability to hold fluid in a body cavity. It is also readily metabolised within the body.

Preferably, a composition of the invention is applied to the appropriate body cavity or area after the operation has been carried out.

Preferably, the composition of the present invention is allowed to remain in the body cavity for a minimum of 2 to 3 days and especially over the period during which fibrin exudation is at a maximum. More preferably, the composition should remain in the body cavity for a period of up to 7 to 8 days in order to allow restoration of non-stick surfaces (mesothelium regeneration).

Preferably, a composition of the invention should be applied to the body cavity in a volume large enough to keep the surfaces apart. For the peritoneum, the volume should preferably be in the range 500-2000 ml and, more preferably, about 1000 ml-1500 ml.

Preferably, the composition should be applied to the appropriate body cavity or area in differing concentrations ideally over a concentration range of 2.5-18% and more ideally over a concentration range of 3-5% and most ideally at about 4% by weight, said concentration range is selected for a specified time span, even more ideally the concentration range is selectively altered over a period of time.

Preferably, the composition should include a concentration of dextrin which is such that the fluid largely holds in place over the period it resides in the cavity. Where a composition includes 4% by weight of dextrin then a suitable dwell period for one infusion might be of the order of 2 to 3 days. A high concentration is liable to cause ingress of fluid. A second infusion at day 3 may extend the total dwell period from 6 to 7 days.

Alternatively, a composition having a dextrin concentration of from 12 to 15% by weight may be used in a smaller volume (perhaps about 750 ml) and will be subject to ingress of fluid. However a single infusion might be sufficient for the full 6 to 7 day period.

Comparing dextrin with dextran, the latter has relatively poor biocompatibility. It is subject to immunological hypersensitivity due to its concentration in lymph nodes and its lack of metabolisability. At best, a dextran solution or suspension will act not so much to separate surfaces and therefore prevent adhesions but simply as a lubricant. Dextrin advantageously serves as an osmotic agent, which can maintain the volume of a solution in the peritoneal cavity. The continued presence of the dextrin solution within the cavity serves to separate tissues which otherwise may adhere to each other.

The use of a solution or suspension or gel formulation of dextrin is also advantageous by comparison with a prior art technique which makes use of synthetic films in the form of patches which are applied to particular areas where maximum damage has occurred. However, in the case of a body cavity, such as the peritoneum, the damage is liable to occur as well at a distance from the operative site, especially in laparoscopy, due to the drying which takes place. In some instances global damage over an area of as much as two square meters can take place.

In responding to a wound, the body causes circulating fibrinogen to form fibrin and it is this production of fibrin which is associated with the formation of adhesions. Calcium ions are required to polymerise fibrinogen to fibrin and, accordingly, a composition of the present invention may include a calcium binding agent such as EDTA or sodium citrate.

A composition of the present invention may include a suitable lubricant such as a phosphospholipid.

A composition of the present invention may include a hyaluronate or glycocosolaminoglycan, a material which is associated with serosal lubrication and which has strong anti-adhesive properties. In this case the dextrin solution or suspension or gel formulation is effective in spreading the hyaluronate throughout the whole peritoneum.

A composition of the present invention may include an antibiotic agent or a material/agent which is associated with preventing an infection or build up of bacteria or foreign bodies or the like. A composition including such a material/agent would be particularly advantageous in prevention or amelioration of pelvic inflammatory disease.

A composition of the present invention may also include a fibrinolytic agent or an analogue thereof, an anti-inflammatory agent or an analogue thereof, dextrin sulphate and/or methylene blue.

The present invention provides a preferred composition comprising an aqueous solution or suspension or gel formulation of dextrin, one or more phosphospholipids and hyaluronate. Such a composition is not only highly effective in preventing adhesions but also has a good shelf life.

Mesothelial secretion of prostacyclin has been demonstrated and this activity enhances the non-stick properties of the mesothelium. The present invention provides a composition comprising dextrin together with prostacyclin or an analogue thereof.

According to a second aspect of the invention there is provided a biocompatible, bioresorbable, and non-toxic post-operative adhesion prevention kit for surgical use in humans or animals, comprising an aqueous solution or suspension or gel formulation of dextrin as hereinbefore described, and optionally or additionally comprising a calcium binding agent as hereinbefore described and/or a suitable lubricant as hereinbefore described and/or prostacyclin or an analogue thereof as hereinbefore described and/or an antibiotic agent as hereinbefore described.

Evidence in Support of the Invention

Protocol

Animals: One hundred thirty, female New Zealand White rabbits, 2.4-2.7 kg, were purchased from Irish Farms (Norco, Calif.) and quarantined in the USC Vivaria for at least 2 days prior to use. Ten rabbits were randomised into thirteen treatment groups prior to initiation of surgery. The rabbits were housed on a 12:12 light:dark cycle with food and water available ad libitum.

Materials: The solutions (7.5% [wt/vol] icodextrin-Lot #98A06G33, 20% [wt/vol] icodextrin-Batch #SP184772 and placebo (electrolyte solution for icodextrin)-Batch #SP184829 were supplied by ML Laboratories Plc. Icodextrin is a [1→4]-α-Glucan having more than 85% of its molecules with molecular weights between 1,640-45,000 with a weight average molecular weight of approximately 20,000. The placebo electrolyte solution contained 5.4 g sodium chloride, 4.5 g sodium lactate, 257 mg calcium chloride, 51 mg magnesium chloride in 1 liter water for injection. The sutures used to close the muscle and skin were 3-0 coated Dexon II suture (Davis and Geck, Manati, PR).

Double Uterine Horn Model: Rabbits were anaesthetised with a mixture of 55 mg/kg ketamine hydrochloride and 5 mg/kg Rompum intramuscularly. Following preparation for sterile surgery, a midline laparotomy was performed. The uterine horns were exteriorised and traumatised by abrasion of the serosal surface with gauze until punctuate bleeding developed. Ischaemia of both uterine horns was induced by removal of the collateral blood supply. The remaining blood supply to the uterine horns was the ascending branches of the utero-vaginal arterial supply of the myometrium. At the end of surgery, 10 to 75 ml (10, 25, 50, 75 ml) of 7.5% or 20% icodextrin, 10 or 75 ml placebo or no treatment (control) was administered. After 7 days, the rabbits were terminated and the percentage of the area of the horns adherent to the various organs was determined. In addition, the tenacity of the adhesions was scored using the following system:

0=No adhesions;
1=Mild, easily dissectable adhesions;
2=Moderate adhesions; non-dissectable, does not tear the organ;
3=Dense adhesions; non-dissectable, tears organ when removed.

In addition an overall score which takes into account all of the above data was given to each rabbit. The following scoring system was used:

0 No adhesions;
0.5+ Light, filmy pelvic adhesions involving only one organ, typically only 1 or 2 small adhesions;
1.0+ Light, filmy adhesions, not extensive although slightly more extensive than 0.5;
1.5+ Adhesions slightly tougher and more extensive than a 1 rating;
2.0+ Tougher adhesions, a little more extensive, uterine horns usually have adhesions to both bowel and bladder;
2.5+ Same as 2, except the adhesions are usually not filmy at any site and more extensive;
3.0+ Tougher adhesions than 2, more extensive, both horns are attached to the bowel and bladder, some movement of the uterus possible;
3.5+ Same as 3, but adhesions slightly more extensive and tougher;
4.0+ Severe adhesions, both horns attached to the bowel and bladder, unable to move the uterus without tearing the adhesions.

The rabbits were scored by two independent observers that were blinded to the prior treatment of the animal. If there was disagreement as to the score to be assigned to an individual animal, the higher score was given.

Statistical Analysis: The tenacity and overall scores were analysed by rank order analysis and analysis of variance on the ranks. The percentage area of the horns involved to the various organs was compared by Student's t test. The data from the incidence of adhesion formation was analysed by Chi square analysis. The comparison with placebo shown on Table 14 was done between the 10 ml placebo group and data from animals which received 10-25 ml of icodextrin or between the 75 ml placebo group and data from animals which received 50 or 75 ml icodextrin.

RESULTS: One rabbit from the group treated with 50 ml 20% icodextrin died postoperatively without evidence of inflammation or oedema at necropsy and was replaced. During the postoperative evaluation of the rabbits, it was noted that several rabbits given the higher volumes of icodextrin had "bulging" abdomens for the first few postoperative days. This occurred in 3 rabbits which received 75 ml or 7.5% icodextrin and 8 rabbits which received 75 ml of 20% icodextrin. The bulging was observed for 24 hours in the rabbits which received 7.5% icodextrin and 48-72 hours in the rabbits which received 20% icodextrin. This bulging was not observed in the group of rabbits which received 75 ml of placebo. No excess fluid was observed in any icodextrin or placebo-treated rabbits at necropsy. One rabbit, which received 75 ml of 20% icodextrin, had a small amount of subcutaneous fluid at necropsy.

The effect of icodextrin on the formation of adhesions in this rabbit model can be found in Tables 1-13. The effect of icodextrin on the incidence of adhesions can be found in Table 14. For each site, the extent and tenacity (tenacity in parentheses) of the adhesions between the horn and that site were given. In the final row of each column (with the exception of the column on the far right), the mean and standard error of the mean for the extent score for each site is given. In the final row of the final column, the mean and standard error of the mean of the ranks is given. If an extent or rank order was reduced compared to control ($p \leq 0.05$), a * is in the appropriate row. At higher volumes (25 to 75 ml) of icodextrin, there was a significant reduction in the formation of adhesions. However, no difference between the 7.5% and 20% solutions was noted in this study. This efficacy is in the absence of inflammation noted with some materials implanted intraperitoneally.

In conclusion results demonstrated that high volumes of icodextrin (both percentages) were highly efficacious in the reduction of adhesion formation in this model with efficacy noted after administration of 50 ml or 75 ml of icodextrin. The lower volumes of icodextrin have less effect and the placebo had no effect on adhesion formation. Thus we have demonstrated that the composition of the present invention is effective in reducing the incidence of post-operative adhesion formation.

TABLE 1

Data from Surgical control Rabbits
% Horn Involved

| Right Horn | | | | Left Horn | | | | |
| --- | --- | --- | --- | --- | --- | --- | --- | --- |
| Bowel | Bladder | Itself | Left | Bowel | Bladder | Itself | Right | Overall |
| 30(2) | 30(2) | 30(1) | 40(1) | 30(2) | 30(2) | 30(1) | 40(1) | 2.5+ |
| 30(1) | 30(1) | 50(2) | 50(2) | 30(1) | 30(1) | 30(1) | 50(2) | 2.5+ |
| 30(2) | 30(1) | 40(2) | 40(2) | 30(2) | 30(2) | 40(2) | 40(2) | 3.0+ |
| 40(1) | 20(1) | 50(2) | 30(1) | 40(1) | 20(1) | 30(1) | 30(1) | 3.0+ |
| 20(1) | 30(1) | 50(2) | 40(2) | 20(1) | 30(1) | 50(2) | 40(2) | 3.0+ |
| 40(1) | 30(1) | 50(1) | 40(1) | 40(1) | 30(1) | 60(1) | 40(1) | 3.5+ |
| 40(1) | — | 50(1) | 40(2) | 40(1) | — | 50(1) | 40(1) | 3.0+ |
| 40(1) | 20(1) | 50(1) | 40(1) | 40(1) | 20(1) | 40(2) | 40(1) | 3.0+ |
| 40(2) | 20(2) | 40(2) | 30(2) | 40(2) | 20(2) | 50(1) | 30(2) | 3.5+ |
| 40(1) | 20(1) | 60(1) | 50(1) | 40(1) | 20(1) | 60(1) | 50(1) | 3.0+ |
| 31 ± 3.7 | 23 ± 3.0 | 47 ± 2.6 | 40 ± 2.1 | 34 ± 3.7 | 23 ± 3.0 | 44 ± 3.7 | 40 ± 2.1 | 111.2 ± 4.0 |

TABLE 2

Data from 10 ml Placebo Rabbits
% Horn Involved

| Right Horn | | | | Left Horn | | | | |
|---|---|---|---|---|---|---|---|---|
| Bowel | Bladder | Itself | Left | Bowel | Bladder | Itself | Right | Overall |
| 30(1) | 20(1) | 50(2) | 30(1) | 30(1) | 20(1) | 40(2) | 30(1) | 2.5+ |
| 50(2) | 50(2) | 60(1) | 30(2) | 50(2) | 50(2) | 60(1) | 30(2) | 3.5+ |
| 40(2) | — | 50(1) | 20(2) | 40(2) | — | 50(1) | 20(2) | 3.0+ |
| 20(1) | — | 30(1) | 20(1) | 20(1) | — | 30(1) | 20(2) | 1.5+ |
| — | 30(2) | 40(1) | 40(2) | — | 30(2) | 40(1) | 40(2) | 2.5+ |
| 50(1) | 20(1) | 40(2) | 30(1) | 50(1) | 20(1) | 50(1) | 30(1) | 3.0+ |
| 30(2) | — | 20(2) | 40(2) | 30(2) | — | 20(2) | 40(2) | 3.0+ |
| 30(2) | — | 30(2) | 40(1) | 30(2) | — | 50(2) | 40(1) | 3.0+ |
| 50(2) | — | 40(1) | 50(2) | 50(2) | — | 40(1) | 50(2) | 3.0+ |
| 30(2) | 20(2) | 30(1) | 40(1) | 30(2) | 20(2) | 50(1) | 40(1) | 2.5+ |
| 33 ± 5.0 | 14 ± 5.4 | 39 ± 3.9 | 34 ± 3.0 | 33 ± 5.0 | 14 ± 5.4 | 43 ± 3.7 | 34 ± 3.1 | 100.7 ± 7.5 |

TABLE 3

Data from 75 ml Placebo Rabbits
% Horn Involved

| Right Horn | | | | Left Horn | | | | |
|---|---|---|---|---|---|---|---|---|
| Bowel | Bladder | Itself | Left | Bowel | Bladder | Itself | Right | Overall |
| 40(2) | 30(2) | 50(2) | 40(2) | 40(20) | 30(2) | 40(3) | 40(2) | 3.5+ |
| — | — | 50(1) | 20(1) | — | — | 40(1) | 20(1) | 2.5+ |
| — | 40(2) | 30(10) | 40(2) | — | 40(2) | 40(2) | 40(2) | 3.0+ |
| 40(1) | 20(1) | 50(1) | 20(1) | 40(1) | 20(1) | 50(1) | 20(1) | 3.0+ |
| 20(1) | — | 40(1) | 20(1) | 20(1) | — | 30(1) | 20(1) | 2.0+ |
| — | 10(1) | 20(1) | 40(1) | — | 10(1) | 40(1) | 40(1) | 2.0+ |
| — | 30.2 | 50(2) | 40(2) | — | 30(2) | 50(2) | 40(2) | 3.0+ |
| 40(1) | 20(1) | 50(1) | 20(1) | 40(1) | 20(1) | 30(1) | 20(1) | 2.5+ |
| 20(1) | — | 60(1) | 50(1) | 20(1) | — | 50(1) | 50(1) | 3.0+ |
| 20(2) | 10(1) | 40(1) | 30(1) | 20(2) | 10(1) | 50(2) | 30(1) | 3.0+ |
| 18 ± 5.5 | 16 ± 4.5 | 44 ± 3.7 | 32 ± 3.6 | 18 ± 5.5 | 16 ± 4.5 | 42 ± 7.9 | 32 ± 3.6 | 100.5 ± 6.8 |

TABLE 4

Data from 10 ml 7.5% Icodextrin Rabbits
% Horn Involved

| Right Horn | | | | Left Horn | | | | |
|---|---|---|---|---|---|---|---|---|
| Bowel | Bladder | Itself | Left | Bowel | Bladder | Itself | Right | Overall |
| 30(1) | 20(1) | 50(1) | 40(1) | 30(1) | 20(1) | 50(1) | 40(1) | 2.5+ |
| 40(1) | 30(1) | 50(1) | 40(2) | 40(1) | 30(1) | 50(1) | 40(2) | 3.0+ |
| 40(1) | 10(1) | 30(1) | 10(1) | 40(1) | 10(1) | 10(1) | 10(1) | 2.0+ |
| 30(1) | 20(1) | 30(2) | 30(1) | 30(1) | 20(1) | 30(2) | 30(1) | 2.5+ |
| — | — | 10(1) | 10(1) | — | — | 10(1) | 10(1) | 1.0+ |
| 40(2) | 20(1) | 50(1) | 30(1) | 40(2) | 20(1) | 50(2) | 30(1) | 3.5+ |
| — | 10(1) | 40(1) | 40(2) | — | 10(1) | 50(1) | 40(2) | 2.5+ |
| — | 30(2) | 30(1) | 40(2) | — | 30(2) | 50(2) | 40(2) | 3.0+ |
| 30(2) | — | 50(1) | 30(1) | 30(2) | — | 40(1) | 30(1) | 2.5+ |
| 30(2) | — | 10(1) | 30(1) | 30(2) | — | 50(1) | 30(1) | 2.5+ |
| 24 ± 5.4 | 14 ± 3.7 | 35 ± 5.0 | 30 ± 3.7 | 24 ± 5.4 | 14 ± 3.7 | 39 ± 5.3 | 30 ± 3.7 | 88.8 ± 9.3* |

TABLE 5

Data from 15 ml 7.5% Icodextrin Rabbits
% Horn Involved

| Right Horn | | | | Left Horn | | | | |
|---|---|---|---|---|---|---|---|---|
| Bowel | Bladder | Itself | Left | Bowel | Bladder | Itself | Right | Overall |
| 20(1) | 10(1) | 40(1) | 40(1) | 20(1) | 10(1) | 40(1) | 40(1) | 2.5+ |
| 10(1) | — | 30(1) | 30(1) | 10(1) | — | 30(1) | 30(1) | 2.0+ |
| 30(2) | 30(2) | 40(1) | 20(1) | 30(2) | 30(2) | 40(1) | 20(2) | 2.5+ |
| 10(1) | 20(1) | 30(1) | 10(1) | 10(1) | 20(1) | 30(1) | 10(1) | 2.0+ |
| 30(1) | 30(1) | 40(1) | 30(1) | 30(1) | 30(1) | 40(1) | 30(1) | 2.5+ |
| 40(1) | 10(1) | 50(1) | 50(1) | 40(1) | 10(1) | 50(1) | 50(1) | 3.0+ |
| — | 20(1) | 30(1) | 20(1) | — | 20(1) | 30(1) | 20(1) | 1.5+ |
| 20(1) | 10(1) | 30(1) | 10(1) | 20(1) | 10(1) | 30(1) | 10(1) | 1.5+ |
| 30(2) | 30(2) | 40(1) | 10(1) | 30(2) | 30(2) | 50(1) | 10(1) | 2.5+ |
| — | 30(1) | 40(1) | 30(2) | — | 30(1) | 50(1) | 30(2) | 2.5+ |
| 19 ± 4.3* | 19 ± 3.5 | 37 ± 2.1* | 25 ± 4.3* | 19 ± 4.3* | 19 ± 3.5 | 39 ± 2.8 | 25 ± 4.3* | 78.2 ± 7.0* |

TABLE 6

Data from 25 ml 7.5% Icodextrin Rabbits
% Horn Involved

| Right Horn | | | | Left Horn | | | | |
|---|---|---|---|---|---|---|---|---|
| Bowel | Bladder | Itself | Left | Bowel | Bladder | Itself | Right | Overall |
| 10(1) | — | 30(1) | 20(1) | 10(1) | — | 30(1) | 20(1) | 1.5+ |
| — | — | 40(1) | — | — | — | 40(1) | — | 1.0+ |
| 10(1) | — | 30(1) | 20(2) | 10(1) | — | 30(1) | 20(1) | 2.0+ |
| 10(1) | — | 30(1) | 10(1) | 10(1) | — | 30(1) | 10(1) | 2.0+ |
| — | — | 10(1) | 10(1) | — | — | — | 10(1) | 1.0+ |
| — | — | 30(1) | — | — | — | 10(1) | — | 1.0+ |
| — | — | 20(1) | 40(1) | — | — | 30(2) | 40(1) | 2.0+ |
| 40(1) | 30(1) | 30(1) | 10(1) | 40(1) | 30(1) | 30(1) | 10(1) | 2.5+ |
| 10(1) | — | 20(1) | 10(1) | 10(1) | — | 30(1) | 10(1) | 1.5+ |
| 30(1) | — | 30(1) | 30(1) | 30(1) | — | 40(1) | 30(1) | 2.0+ |
| 11 ± 4.3* | 3 ± 3.0* | 27 ± 2.6* | 15 ± 4.0* | 11 ± 4.3* | 3 ± 3.0* | 27 ± 3.0* | 15 ± 4.0* | 50.6 ± 7.6* |

TABLE 7

Data from 50 ml 7.5% Icodextrin Rabbits
% Horn Involved

| Right Horn | | | | Left Horn | | | | |
|---|---|---|---|---|---|---|---|---|
| Bowel | Bladder | Itself | Left | Bowel | Bladder | Itself | Right | Overall |
| — | — | 30(1) | 10(1) | — | — | 30(1) | 10(1) | 1.0+ |
| — | — | 20(1) | 10(1) | — | — | 20(1) | 10(1) | 1.0+ |
| 10(1) | — | 30(1) | — | 10(1) | — | 30(1) | — | 1.0+ |
| — | — | 20(1) | 10(1) | — | — | 20(1) | 10(1) | 1.0+ |
| — | — | 30(2) | 10(1) | — | — | 30(2) | 10(1) | 1.5+ |
| 20(1) | 10(1) | 10(1) | — | 20(1) | — | — | — | 1.0+ |
| — | 10(1) | 30(2) | 40(2) | — | 10(1) | 30(2) | 40(2) | 2.5+ |
| 30(1) | — | 40(1) | 10(1) | 30(1) | — | 10(1) | 10(1) | 2.0+ |
| 10(1) | 10(2) | 10(1) | 10(1) | 10(1) | 10(2) | 10(1) | 10(1) | 1.5+ |
| — | — | 20(1) | 30(1) | — | — | 40(1) | 30(1) | 1.5+ |
| 7 ± 3.4* | 3 ± 1.5* | 24 ± 3.1* | 13 ± 4.0* | 7 ± 3.4* | 2 ± 1.3* | 22 ± 3.9* | 13 ± 4.0* | 39.4 ± 7.4* |

TABLE 8

Data from 75 ml 7.5% Icodextrin Rabbits
% Horn Involved

| Right Horn | | | | Left Horn | | | | |
|---|---|---|---|---|---|---|---|---|
| Bowel | Bladder | Itself | Left | Bowel | Bladder | Itself | Right | Overall |
| — | — | — | — | — | — | 10(1) | — | 0.5+ |
| 10(2) | — | 30(1) | — | 10(2) | — | 20(1) | — | 1.0+ |
| — | — | — | — | — | 10(1) | 30(1) | — | 0.5+ |
| 10(1) | 10(1) | 40(1) | — | 10(1) | 10(1) | — | — | 1.5+ |
| 20(2) | — | 30(1) | — | 20(2) | — | — | — | 1.0+ |
| — | — | 10(1) | — | — | — | 50(1) | — | 1.0+ |
| 10(1) | 20(1) | — | 10(1) | 10(1) | 20(1) | 10(1) | 10(1) | 1.5+ |
| — | — | 20(1) | 10(1) | — | — | 30(1) | 10(1) | 1.0+ |
| — | 10(1) | 10(1) | — | — | 10(1) | 10(1) | — | 1.0+ |
| — | — | 20(1) | 20(1) | — | — | 20(1) | 20(1) | 1.0+ |
| 5 ± 2.2* | 4 ± 2.2* | 16 ± 4.5* | 4 ± 2.2* | 5 ± 2.2* | 5 ± 2.2* | 18 ± 4.9* | 4 ± 2.2* | 22.5 ± 4.2* |

TABLE 9

Data from 10 ml 20% Icodextrin Rabbits
% Horn Involved

| Right Horn | | | | Left Horn | | | | |
|---|---|---|---|---|---|---|---|---|
| Bowel | Bladder | Itself | Left | Bowel | Bladder | Itself | Right | Overall |
| 20(2) | — | 50(2) | 30(2) | 20(2) | — | 50(2) | 30(2) | 3.0+ |
| 10(1) | — | 10(1) | 10(1) | 10(1) | — | 50(1) | 10(1) | 2.0+ |
| 40(1) | — | 50(2) | 30(1) | 40(1) | — | 40(1) | 30(1) | 2.5+ |
| 40(1) | 20(1) | 40(1) | 30(2) | 40(1) | 20(1) | 30(1) | 30(2) | 2.5+ |
| — | 20(1) | 10(1) | — | — | 20(1) | 20(1) | — | 1.0+ |
| 30(2) | — | 40(1) | 30(1) | 30(2) | — | 30(1) | 30(1) | 2.5+ |
| 30(1) | 20(2) | 40(1) | 40(1) | 30(1) | 20(2) | 10(1) | 40(1) | 2.5+ |
| 10(1) | — | 50(1) | 20(1) | 10(1) | — | 30(1) | 20(1) | 2.0+ |
| 20(1) | 10(1) | 40(1) | 40(1) | 20(1) | 10(1) | 30(1) | 40(1) | 2.5+ |
| 20(1) | — | 20(1) | 20(1) | 20(1) | — | 40(2) | 20(1) | 2.0+ |
| 22 ± 4.2 | 7 ± 3.0* | 35 ± 5.0* | 25 ± 4.0* | 22 ± 4.2 | 7 ± 3.0* | 33 ± 4.0 | 25 ± 4.0* | 78 ± 7.9* |

TABLE 10

Data from 15 ml 20% Icodextrin Rabbits
% Horn Involved

| Right Horn | | | | Left Horn | | | | |
|---|---|---|---|---|---|---|---|---|
| Bowel | Bladder | Itself | Left | Bowel | Bladder | Itself | Right | Overall |
| — | — | 50(1) | 50(1) | — | — | 50(1) | 50(1) | 2.5+ |
| 20(1) | 20(1) | 20(1) | 20(1) | 20(1) | 20(1) | 20(1) | 20(1) | 2.0+ |
| — | 30(2) | 50(1) | 30(1) | — | 30(2) | 20(1) | 30(1) | 2.5+ |
| 20(1) | 20(1) | 40(1) | 30(1) | 20(1) | 20(1) | 40(1) | 30(1) | 2.0+ |
| 30(1) | 20(1) | 40(1) | 20(1) | 30(1) | 20(1) | 40(1) | 20(1) | 2.0+ |
| 40(2) | 30(2) | 50(1) | 50(1) | 40(2) | 30(2) | 50(1) | 50(1) | 3.0+ |
| 20(1) | — | 20(1) | — | — | — | — | — | 0.5+ |
| — | — | — | 10(1) | — | — | — | 10(1) | 0.5+ |
| — | 20(1) | 10(1) | 10(1) | — | 20(1) | 20(1) | 10(1) | 1.5+ |
| 30(1) | 30(1) | 40(1) | 40(1) | 20(1) | 30(1) | 40(1) | 30(1) | 2.5+ |
| 16 ± 4.8* | 17 ± 4.0 | 32 ± 5.7 | 25 ± 5.2* | 14 ± 5.0* | 17 ± 4.0 | 28 ± 5.9 | 25 ± 5.2* | 61.3 ± 11.6* |

TABLE 11

Data from 25 ml 20% Icodextrin Rabbits
% Horn Involved

| Right Horn | | | | Left Horn | | | | |
|---|---|---|---|---|---|---|---|---|
| Bowel | Bladder | Itself | Left | Bowel | Bladder | Itself | Right | Overall |
| 20(1) | — | — | 10(1) | 20(1) | — | 40(2) | 10(1) | 1.5+ |
| 20(1) | 20(1) | 40(1) | — | — | — | 30(1) | — | 1.5+ |
| 10(1) | — | 40(1) | 10(1) | 10(1) | — | 30(1) | 10(1) | 1.5+ |
| 30(1) | — | 40(1) | — | 30(1) | — | 10(1) | — | 1.5+ |
| — | — | 10(1) | 10(1) | — | — | 10(1) | 10(1) | 1.0+ |
| 10(1) | — | 10(1) | 10(1) | 10(1) | 20(1) | 20(1) | 10(1) | 2.0+ |
| 20(2) | — | 30(1) | 40(2) | 20(2) | — | 30(1) | 40(2) | 2.5+ |
| — | — | 20(1) | 20(1) | — | — | 50(1) | 20(1) | 1.5+ |
| — | — | — | — | — | — | 10(1) | — | 0.5+ |
| — | 20(1) | 10(1) | — | — | 20(1) | — | 20(1) | 1.0+ |
| 11 ± 3.5* | 6 ± 3.1* | 20 ± 5.2 | 10 ± 3.0* | 9 ± 3.5* | 4 ± 2.7* | 25 ± 4.3* | 10 ± 3.9* | 42.5 ± 7.5* |

TABLE 12

Data from 50 ml 20% Icodextrin Rabbits
% Horn Involved

| Right Horn | | | | Left Horn | | | | |
|---|---|---|---|---|---|---|---|---|
| Bowel | Bladder | Itself | Left | Bowel | Bladder | Itself | Right | Overall |
| — | — | 10(1) | — | — | — | — | — | 0.5+ |
| 10(1) | — | 10(1) | — | — | — | 20(2) | — | 1.0+ |
| 20(1) | — | 20(1) | 10(1) | 20(1) | — | 10(1) | 10(1) | 1.5+ |
| — | 10(1) | — | — | — | — | — | — | 0.5+ |
| — | — | 10(1) | 10(1) | — | — | 20(1) | 10(1) | 1.0+ |
| 30(1) | — | 20(1) | 10(1) | 30(1) | — | 20(1) | 10(1) | 1.5+ |
| — | 10(1) | — | 10(1) | — | 10(1) | 20(1) | 10(1) | 1.5+ |
| — | 20(1) | 40(1) | 30(1) | — | 20(1) | 10(1) | 30(1) | 2.0+ |
| — | 30(1) | 40(1) | 10(1) | — | 30(1) | 20(1) | 10(1) | 2.0+ |
| — | 30(2) | 30(1) | 20(1) | — | 30(2) | 30(2) | 20(1) | 2.0+ |
| 6 ± 3.4 | 10 ± 3.9* | 18 ± 4.7* | 10 ± 3.0 | 5 ± 3.4* | 9 ± 4.1* | 15 ± 3.1* | 10 ± 3.0* | 38.4 ± 7.6* |

TABLE 13

Data from 75 ml 20% Icodextrin Rabbits
% Horn Involved

| Right Horn | | | | Left Horn | | | | |
|---|---|---|---|---|---|---|---|---|
| Bowel | Bladder | Itself | Left | Bowel | Bladder | Itself | Right | Overall |
| — | — | 10(1) | 10(1) | — | — | 20(2) | 10(1) | 1.0+ |
| — | — | — | — | — | — | 30(1) | — | 0.5+ |
| — | — | 30(1) | 10(1) | — | — | 30(1) | 10(1) | 1.0+ |
| 20(1) | 40(1) | 10(1) | — | 20(1) | 40(1) | 10(1) | — | 2.0+ |
| — | 10(1) | 30(1) | 10(1) | — | 10(1) | 30(1) | 10(1) | 1.5+ |
| 10(1) | 10(1) | 20(1) | 30(1) | 10(1) | 10(1) | 20(1) | 30(1) | 1.5+ |
| — | 30(1) | 10(1) | 10(1) | — | 30(1) | 10(1) | 10(1) | 1.5+ |
| — | — | 40(1) | 10(1) | — | — | 20(1) | 10(1) | 1.5+ |
| — | — | 10(1) | 20(1) | — | — | — | 20(1) | 1.0+ |
| — | — | 10(1) | — | 20(1) | — | — | — | 0.5+ |
| 3 ± 2.1* | 9 ± 4.5* | 17 ± 4.0* | 10 ± 3.0* | 5 ± 2.7* | 9 ± 4.6* | 17 ± 3.7* | 10 ± 3.0* | 31.7 ± 6.3* |

TABLE 14

Incidence of Adhesion Formation

| | #Sites Free/ # Possible | % Adhesion Free | p Value Control | p Value Placebo |
|---|---|---|---|---|
| Control | 2/80 | 2.5 | | |
| 10 ml Placebo | 12/80 | 15.0 | 0.012 | |
| 75 ml Placebo | 14/80 | 17.5 | 0.004 | |
| 10 ml 7.5% Icodextrin | 12/80 | 15.0 | 0.012 | 1.00 |
| 15 ml 7.5% Icodextrin | 6/80 | 7.5 | 0.277 | 0.211 |
| 25 ml 7.5% Icodextrin | 31/80 | 38.8 | 0.000 | 0.001 |
| 50 ml 7.5% Icodextrin | 32/80 | 40.0 | 0.000 | 0.003 |
| 75 ml 7.5% Icodextrin | 44/80 | 55.0 | 0.000 | 0.000 |
| 10 ml 20% Icodextrin | 16/80 | 20.0 | 0.001 | 0.533 |
| 15 ml 20% Icodextrin | 20/80 | 25.0 | 0.000 | 0.167 |
| 25 ml 20% Icodextrin | 34/80 | 42.5 | 0.000 | 0.000 |
| 50 ml 20% Icodextrin | 36/80 | 45.0 | 0.000 | 0.000 |
| 75 ml 20% Icodextrin | 36/80 | 45.0 | 0.000 | 0.000 |

The invention claimed is:

1. A method of treating a patient to reduce, in a post-operative period following surgery involving a body cavity, the incidence of post-operative adhesions in the body cavity, comprising treating said patient prior to said post-operative period by providing a single introduction into the body cavity of an aqueous formulation comprising a polysaccharide dextrin in an amount effective to reduce the incidence of said post-operative adhesions, wherein the dextrin is unsubstituted and the dextrin contains more than 15% of polymers with a degree of polymerization (DP) greater than 12, wherein the aqueous formulation that is introduced prior to said post-operative period provides said treating, and wherein the aqueous formulation remains in the body cavity for a minimum of 2 days.

2. A method according to claim 1 wherein said aqueous formulation is applied to the appropriate body cavity after a surgical operation has been carried out.

3. A method according to claim 1 wherein the aqueous formulation is applied to the body cavity in a volume in the range of 500 ml-2000 ml.

4. A method according to claim 3 wherein the aqueous formulation is applied to the body cavity in a volume in the range of 1000 ml-1500 ml.

5. A method according to claim 1 wherein the dextrin in the aqueous formulation applied to the body cavity is present in a concentration range of 2.5-18% weight to volume of the aqueous formulation.

6. A method according to claim 5 wherein the dextrin in the aqueous formulation applied to the appropriate body cavity is present in a concentration range of 3-5% weight to volume of the aqueous formulation.

7. A method according to claim 6 wherein the dextrin in the aqueous formulation applied to the appropriate body cavity is present in an amount of about 4% weight to volume of the aqueous formulation.

8. A method according to claim 1 wherein the body cavity is a peritoneal cavity.

9. The method of claim 7 wherein the body cavity is a peritoneal cavity.

10. The method of claim 1 wherein the aqueous formulation is introduced into the body cavity when the operation is an abdominal operation.

11. The method of claim 1 wherein the aqueous formulation is introduced into the body cavity when the operation is a gynecological operation.

12. The method of claim 1 wherein the aqueous formulation remains in the body cavity for a minimum of 3 days.

13. The method of claim 1 wherein the aqueous formulation remains in the body cavity for up to 7 days.

14. The method of claim 1 wherein the aqueous formulation remains in the body cavity for up to 8 days.

15. A method of treating a patient to reduce, in a post-operative period following surgery involving a body cavity, the incidence of post-operative adhesions in the body cavity, comprising treating said patient prior to said post-operative period by providing a single introduction into the body cavity of an aqueous formulation comprising a polysaccharide dextrin in an amount effective to reduce the incidence of said post-operative adhesions, wherein the dextrin is unsubstituted and the dextrin contains more than 15% of polymers with a degree of polymerization (DP) greater than 12, wherein the aqueous formulation that is introduced prior to said post-operative period provides said treating and wherein:
   the dextrin is applied to the body cavity in an amount of about 4% weight to volume of the aqueous formulation; and
   the aqueous formulation is administered intraperitoneally, and wherein the aqueous formulation remains in the body cavity for a minimum of 2 days.

16. The method of claim 15 wherein the body cavity is a peritoneal cavity.

17. The method of claim 15 wherein the aqueous formulation is introduced into the body cavity after surgery in an abdominal operation.

18. The method of claim 15 wherein the aqueous formulation remains in the body cavity for a minimum of 3 days.

19. The method of claim 15 wherein the aqueous formulation remains in the body cavity for up to 7 days.

20. The method of claim 15 where in the aqueous formulation remains in the body cavity for up to 8 days.

21. A method of treating a patient to reduce, in a post-operative period following surgery involving a body cavity, the incidence of post-operative adhesions in the body cavity, comprising:
   (a) treating said patient prior to said post-operative period by provide a single introduction into the body cavity of an aqueous formulation comprising a polysaccharide dextrin in an amount effective to reduce the incidence of said post-operative adhesions, wherein the dextrin is unsubstituted and the dextrin contains more than 15% of polymers with a degree of polymerization (DP) greater than 12 and acts as an osmotic agent to maintain a volume of the aqueous formulation in the body cavity serving to separate tissues which otherwise may adhere to each other, and wherein the aqueous formulation is a solution in the body cavity; and
   (b) allowing the aqueous formulation to remain in the body cavity for at least 2 days, wherein the aqueous formulation that is introduced prior to said post-operative period provides said treating.

22. The method of claim 21 wherein body cavity is a peritoneal cavity.

23. The method of claim 21 wherein the aqueous formulation is introduced into the body cavity when the operation is an abdominal operation.

24. The method of claim 21 wherein the aqueous formulation is introduced into the body cavity when the operation is a gynecological operation.

25. The method of claim 21 wherein said aqueous formulation is applied to the appropriate body cavity after a surgical operation has been carried out.

26. The method of claim 21 wherein the aqueous formulation is applied to the body cavity in a volume in the range of 500 ml-2000 ml.

27. The method of claim 21 wherein the aqueous formulation is applied to the body cavity in a volume in the range of 1000 ml-1500 ml.

28. The method of claim 21 wherein the dextrin is applied to the appropriate body cavity in an amount of about 4% weight to volume of the aqueous formulation.

29. The method of claim 28 wherein the body cavity is a peritoneal cavity.

30. The method of claim 21 where the aqueous formulation remains in the body cavity for a minimum of 3 days.

31. The method of claim 21 wherein the aqueous formulation remains in the body cavity for up to 7 days.

32. The method of claim 21 wherein the aqueous formulation remains in the body cavity for up to 8 days.

33. A method of treating a patient to reduce, in a post-operative period following surgery involving a body cavity, the incidence of post-operative adhesions in the body cavity, comprising treating said patient prior to said post-operative period by providing a single introduction into the body cavity of an aqueous formulation comprising a polysaccharide dextrin in an amount effective to reduce the incidence of said post-operative adhesions, wherein the dextrin is unsubstituted and the dextrin contains more than 15% of polymers with a degree of polymerization (DP) greater than 12 and acts as an osmotic agent to maintain a volume of the aqueous formulation in the body cavity serving to separate tissues which otherwise may adhere to each other, and wherein the aqueous formulation is a solution in the body cavity administered under surgical conditions wherein the aqueous formulation that is introduced prior to said post-operative period provides said treating, wherein the aqueous formulation remains in the body cavity for a minimum of 2 days.

34. The method of claim 33 wherein the body cavity is a peritoneal cavity.

35. The method of claim 33 wherein the surgical condition is an abdominal surgery.

36. The method of claim 33 wherein the surgical condition is a gynecological surgery.

37. The method of claim 33 wherein said aqueous formulation is applied to the appropriate body cavity after a surgical operation has been carried out.

38. The method of claim 33 wherein the aqueous formulation is applied to the body cavity in a volume in the range of 500 ml-2000 ml.

39. The method of claim 33 wherein the aqueous formulation is applied to the body cavity in a volume in the range of 1000 ml-1500 ml.

40. The method of claim 33 wherein the dextrin is applied to the appropriate body cavity in an amount of about 4% weight to volume of the aqueous formulation.

41. The method of claim 40 wherein the body cavity is a peritoneal cavity.

42. The method of claim 33 wherein the aqueous formulation remains in the body cavity for a minimum of 3 days.

43. The method of claim 33 wherein the aqueous formulation remains in the body cavity for up to 7 days.

44. The method of claim 33 where in the aqueous formulation remains in the body cavity for up to 8 days.

* * * * *